(12) United States Patent
Ying et al.

(10) Patent No.: US 8,895,525 B2
(45) Date of Patent: Nov. 25, 2014

(54) PREVENTING HYALURONAN-MEDIATED TUMORIGENETIC MECHANISMS USING INTRONIC RNAS

(75) Inventors: Shao-Yao Ying, San Marino, CA (US); Shi-Lung Lin, Arcadia, CA (US)

(73) Assignee: University of Southern California, Los Angeles, CA (US)

( * ) Notice: Subject to any disclaimer, the term of this patent is extended or adjusted under 35 U.S.C. 154(b) by 390 days.

(21) Appl. No.: 12/740,334

(22) PCT Filed: Oct. 29, 2008

(86) PCT No.: PCT/US2008/081621
§ 371 (c)(1),
(2), (4) Date: Jul. 26, 2010

(87) PCT Pub. No.: WO2009/058893
PCT Pub. Date: May 7, 2009

(65) Prior Publication Data
US 2010/0298416 A1 Nov. 25, 2010

Related U.S. Application Data

(60) Provisional application No. 60/983,456, filed on Oct. 29, 2007.

(51) Int. Cl.
*A61K 48/00* (2006.01)
*C07H 21/02* (2006.01)
*C07H 21/04* (2006.01)

(52) U.S. Cl.
USPC .......................... 514/44; 536/23.1; 536/24.5

(58) Field of Classification Search
None
See application file for complete search history.

(56) References Cited

U.S. PATENT DOCUMENTS

| 2007/0142313 A1 | 6/2007 | Srivastiva et al. |
| 2007/0161004 A1 | 7/2007 | Brown et al. |
| 2009/0131348 A1* | 5/2009 | Labourier et al. .............. 514/44 |

* cited by examiner

*Primary Examiner* — Amy Bowman
(74) *Attorney, Agent, or Firm* — DLA Piper LLP (US)

(57) ABSTRACT

Patterns of microRNA (miRNA) expression are correlated to the degrees of tumor cell differentiation in human prostate cancer. MiRNAs can complementarily bind to either oncogenes or tumor suppressor genes, resulting in targeted gene silencing and thus changes of cellular tumorigenicity. Using miRNA microarray analysis, 8 down-regulated and 3 up-regulated known miRNAs in androgen-independent human prostate cancer cell lines, such as LNCaP C4-2B and PC3, compared to those androgen-dependent cell lines, such as LNCaP and PC3-AR9 were consistently detected. Fluorescent in-situ hybridization assays in human prostate cancer tissue arrays containing sixty patients at different stages also showed the same miRNA expression patterns in hormone-refractory prostate carcinomas (HRPC) compared to androgen-sensitive non-cancerous prostate epithelium. In-vitro tumorigenecity assays using one of the identified miRNAs, mir-146a, were performed to provide validation of its function in prostate cancer. Gain-of-function transfection of mir-146a markedly suppressed its targeted ROCK1 gene expression in androgen-independent PC3 cells, consequently resulting in reduced cancer cell proliferation, invasion and metastasis to human bone marrow endothelial cell monolayers. Since ROCK1 is the key kinase for activating hyaluronan-mediated HRPC transformation in vivo and in PC3 cells, mir-146a should function as a tumor-suppressor gene in modulating the ROCK1-associated tumorigenecity.

8 Claims, 4 Drawing Sheets

PREVENTING HYALURONAN-MEDIATED TUMORIGENETIC MECHANISMS USING INTRONIC RNAS

CROSS-REFERENCE TO THE RELATED APPLICATIONS

This application is a national stage of international application No. PCT/US08/81621, filed on Oct. 29, 2008 and claims the benefit of priority under 35 USC 119 to U.S. Provisional Application No. 60/983,456, filed on Oct. 29, 2007, the entire contents of which are incorporated herein by reference.

STATEMENT REGARDING FEDERALLY SPONSORED RESEARCH OR DEVELOPMENT

This invention was made with government support under Contract No. CA-85722 awarded by the National Institutes of Health. The government has certain rights in the invention.

FIELD OF THE INVENTION

The present invention relates to preventing hyaluronan-mediated tumorigenetic mechanisms using intronic RNAs.

BACKGROUND OF THE INVENTION

Hormone-refractory prostate cancer (HRPC) is a leading cause of aging-related cancer and death in men. Normal prostatic cell growth is controlled by androgens, whereas prostate cancer often occurs when this control is disturbed as one ages. The mainstay treatment of androgen-dependent prostate cancer is to remove androgen stimulation by surgery or by hormonal therapy, which, although is temporarily effective, eventually results in a deadly androgen-independent cancer transformation. To understand this cancer transformation mechanism, several microarray studies have been performed to profile specific gene and microRNA expression patterns in relation to HRPC progression in vivo (1, 2, 3). These studies all showed that expression of non-coding RNAs was highly correlated to the degree of tumor differentiation in human prostate cancer. However, in the absence of tissue-specific expression patterning analysis and functional validation, the functions of these microarray-identified non-coding RNAs have not been confirmed by experiments.

MicroRNA (miRNA) is an abundant class of small non-coding RNAs sized about 17 to 25 nucleotides in length, capable of degrading mRNA or suppressing translation of the targeted genes with high sequence complementarity. In cancers, they are involved in suppression of oncogenes or tumor suppressor genes via complementary binding to their targeted gene transcripts, resulting in gene silencing, that results in changes in cellular tumorigenecity (4). Given that cancer progression is a multi-step process involving changes of various oncogene and tumor suppressor gene expressions, the approach to define a certain miRNA function in modulating these tumorigenetic changes can be complicated by the fact that most miRNAs have several or even several tens of targets, moreover, some of which are targeted more strongly than others. Although current computer programs provide a easy way to predict the potential miRNA targets as well as the possible base-pairs of miRNA-target binding, a simple search for sequence complementarity is not sufficient to pin-point the exact interaction between a specific miRNA and its real target(s).

SUMMARY OF THE INVENTION

To overcome the above problem, the inventors adopted a new approach, in which tissue-specific (i.e., human prostate cancer tissue) and stage-specific in vivo expression patterns of the microarray-identified miRNAs are confirmed by fluorescent in-situ hybridization (FISH). Then vector-based over-expression of each identified miRNA was performed to observe the individual miRNAs effect on human prostate cancer cell growth in vitro. By this means, the inventors are not only able to correlate the tissue-specific miRNA expression patterns with the cancer stages, but also provided a functional assay to understand the role of each microarray-identified miRNA in cancer progression.

Previous miRNA microarray studies have shown abundant information about the over-expression of miRNAs in HRPC versus benign prostatic hyperplasia (BPH); however, many of the results among these studies were inconsistent with each other. Such variations might result from the limited patient samples used in the study or the complications of the selected cancer samples. To prevent these in vivo variations, the inventors used the same microarray approach but analyzed the miRNA that were differentially expressed miRNAs between human HRPC cell lines, such as LNCaP C4-2B and PC3, and their opposite counterpart androgen-dependent cell lines, such as LNCaP and PC3-AR9. Since these human prostate cancer cell lines have been known to preserve relatively high similarities to certain stages of human prostate cancers, they might provide results that are more consistent for providing insight into the identification of miRNAs whose expression correlates with prostate cancer progression. Based on this strategy, the inventors have established a simple experimental procedure for connecting the miRNAs found in vitro to their functions in vivo. The present invention demonstrates that excessive miRNA-146a expression was exclusively found in androgen-dependent LNCaP and PC3-AR9 cell lines and over-expression of miRNA-146a in the opposite counterpart androgen-independent PC3 cell line greatly reduced its tumorigenecity in terms of cancer cell proliferation, invasion and metastasis to human bone marrow endothelial cell layers.

The miRNA family of mir-146a and mir-146b was discovered in mouse and shares approximately 91% homology with RNA that is approximately 22 nucleotides long (5). Both mir-146a and mir-146b are identical to their human counterparts, indicating that they might target the same genes conserved in humans. The, ROCK1 gene was recently identified and found to be highly involved in HRPC transformation and metastasis in vivo as well as in HRPC-derived PC3 cells (6). In over 70% of advanced prostate cancer patients, hyaluronan (HA), an extracellular disaccharide matrix polymer, frequently bound to its receptors, such as CD168 and/or CD44, and then stimulated the activation of Rho-activated protein kinase (ROCK)-mediated signal transduction pathways. Active ROCK had two tumorigenetic functions. First, it increased myosin light chain (MLC) phosphorylation and actin/myosin-coupled contraction, which might enhance cancer migration and metastasis (7, 8). Second, HA-activated ROCK could phosphorylate its linker molecule, Gab1, and promote the membrane localization of both Gab1 and CD168/CD44 for activation of phosphatidylinositol-(3,4,5) $P_3$ kinases (PI3K), which then further converted phosphatidylinositol (PtdIns)-(4,5)$P_2$ to PtdIns-(3,4,5)$P_3$ (IP3), subsequently leading to the activation of Akt/mTOR/eIF4E signal transduction (6). Activation of the Akt/mTOR/eIF4E signaling has been often reported to increase malignant transformation and drug resistance of HRPC (9, 10).

The inventors' previous studies have shown that HA-mediated CD168 signaling is one of the major stimuli for HRPC transformation via the ROCK-PI3K-Akt/TOR-eIF4E signaling cascade. Activation of this signal transduction pathway is directly related to the clinical staging, cell proliferation, cell invasion, and metastasis of HRPC in vitro as well as in vivo. The present invention further demonstrates that mir-146a may function as a tumor-suppressor gene to inhibit the activation of HA-mediated CD168/ROCK signaling in human prostate epithelium, providing what is believed to be the first insight into the mechanism of mir-146a. This may lead to the development of therapies against HRPC transformation.

The above-mentioned and other features of this invention and the manner of obtaining and using them will become more apparent, and will be best understood, by reference to the following description, taken in conjunction with the accompanying drawings. The drawings depict only typical embodiments of the invention and do not therefore limit its scope.

DETAILED DESCRIPTION OF THE INVENTION

Figure 1:
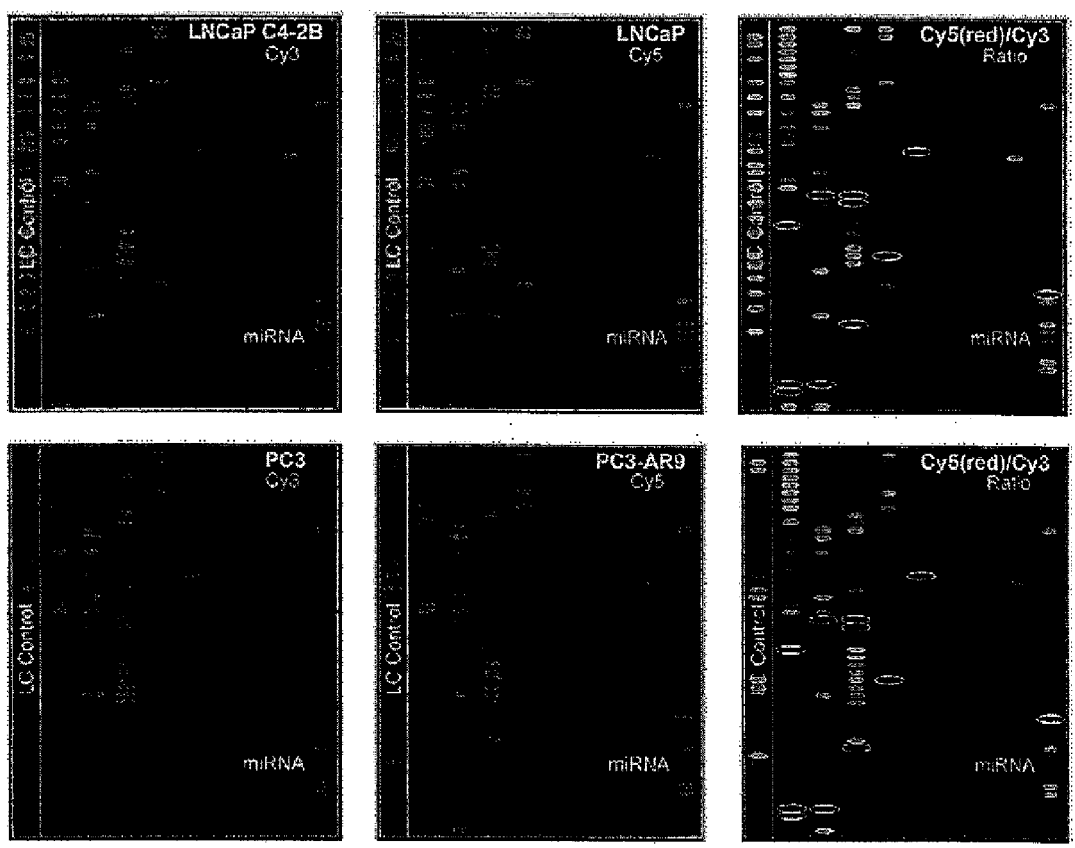
FIG. 1. MicroRNA microarray analyses of androgen-independent human prostate cancer cell lines, such as LNCaP C4-2B and PC3 (labeled by Cy3), compared to the androgen-dependent cell lines, such as LNCaP and PC3-AR9 (labeled by Cy5), respectively ($p<0.01$, $n=3$). Comparison of differentially expressed miRNAs in LNCaP versus C4-2B cells (upper three panels) and PC3-AR9 versus PC3 cells (lower three panels) shown 11 consistent miRNA alterations (white circles in the most right two panels), including up-regulated mir-184, mir-361 and mix-424 (green dots) and down-regulated mir-19b, mir-29b, mir-128b, mir-146a, mix-146b, mir-221, mir-222 and mir-663 (red clots). Each of the four blue panels represented the individual miRNA expression pattern in each cell line, showing miRNA expression from low abundant (blue-green) to high abundant (red) levels.

Abbreviations miRNA, microRNA; HRPC, hormone-refractory prostate cancer; HA, hyaluronan; CD168 (RHAMM), receptor for hyaluronan-mediated motility; ROCK, Rho-activated protein kinase; PI3K, phosphatidylinositol-(3,4,5)$P_3$ kinase; eIF4E, cap-dependent eukaryotic initiation factor 4E; FISH, fluorescent in-situ hybridization; hBMEC, human bone marrow endothelial cell.

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

Materials and Methods

Cell Culture and Treatments

Human prostate cancer cell lines, LNCaP and PC3 cells were obtained from the American Type Culture Collection (ATCC, Rockville, Md.), and the C4-2B and PC3-AR9 cell lines were provided by Dr. Gerhard Coetzee at University of Southern California and Dr. Chawnshang Chang at University of Rochester Medical Center, respectively. All cell lines were grown in phenol red-free DMEM with 10% charcoal-stripped FBS and 1% gentamycin as reported (6). In addition, a mir-146a-mediated, ROCK1-depleted PC3 cell line, namely PC3-mir146a, was generated using a cytomegalovirus (CMV) promoter-driven intronic miRNA expression vector system as reported (11, 12). To deplete ROCK1 expression in PC3 cells, a precursor has-mir-146a sequence, encoding 5'-CCGAUGUGUA UCCUCAGCUU UGAGAACUGA AUUCCAUGGG UUGUGUCAGU GUCAGACCUC UGAAAUUCAG UUCUUCAGCU GGGAUAUCUC UGU-CAUCGU-3', was transfectively expressed and expected to target against the ROCK1 gene nucleotide 1504-1525 region (accession number NM005406), which contained a Rho-binding domain required for ROCK kinase activation. For miRNA knock-in assays, the designed vectors were liposomally encapsulated in a FuGENE reagent (Roche, Indianapolis, Iowa) and applied to cell cultures at 40% confluency. After 24-h incubation, positively transfected cells were isolated for sub-culturing, using flow cytometry selection with anti-RGFP monoclonal antibody (Clontech, Palo Alto, Calif.) as reported (6). The resulting ROCK1-knockdown efficacy was determined by Northern blot and Western blot analyses as reported (6). For further HA stimulation, low molecular weight HA at 400 μg/ml was added to the cell cultures at about 40% confluency as reported (6).

MicroRNA Microarray Analysis

Human prostate cancer cell lines, LNCaP, LNCaP C4-2B, PC3 and PC3-AR9, were prepared as described previously. At 70% confluency, small RNAs from each cell culture line were isolated using the mirVana™ miRNA isolation kit (Ambion, Inc., Austin, Tex.), following the manufacturer's suggestion. The purity and quantity of the isolated small RNAs were assessed using 1% formaldehyde-agarose gel electrophoresis and spectrophotometer measurement (Bio-Rad, Hercules, Calif.), and then submitted to LC Sciences (San Diego, Calif.) for miRNA microarray analysis. Each microarray chip hybridized a single sample labeled with either Cy3 or Cy5 or a pair of samples labeled with Cy3 and Cy5, respectively. Background subtraction and normalization were performed. For a dual sample assay, a p-value calculation was performed and a list of differentially expressed transcripts more than 3-fold was produced.

Fluorescent In-Situ Hybridization (FISH) of Tissue Arrays

Human prostate cancer tissue arrays were obtained from Imgenex (San Diego, Calif.). FISH kits were purchased from Ambion Inc. and performed according to the manufacturer's suggestions. The inventors used synthetic locked nucleic acid (LNA) probes (Sigma-Genosys, St. Louis, Mo.) directed against the mature mir-184 and mir-146a sequences, respectively. The LNA-modified DNA oligonucleotide was a high-affinity RNA analogue with a bicyclic furanose unit locked in an RNA-mimicking sugar conformation, which provided strong hybridization affinity towards complementary single-stranded RNA molecules. In experiments, tissue arrays were dewaxed in xylene, rehydrated through an ethanol series (100%, 95%, 90%, 80%, 70%. 50%, 30%) and postfixed in 4% paraformaldehyde for 30 min. Then, the arrays were digested with proteinase K (10 μg/ml, Roche) for 5 min, refixed with 4% paraformaldehyde and washed in Tris/glycine buffer. After that, the arrays were hybridized overnight at 60° C. within cloverslip chambers in in-situ hybridization buffer (40% formamide, 5×SSC, 1×Denhard's solution. 100 μg/ml salmon testis DNA, 100 μg/ml tRNA), containing 1 ng/μl of fluorescin-labeled LNA probes. After post-hybridization washes once with 5×SSC and once with 0.5×SSC at 25° C. for 1 h, positive results were observed under a 100× microscope with whole field scanning and recorded at 100× and 400× magnification (Nikon 80i microscopic quantitation system).

Fluorescent Cytochemical and Immunocytochemical Staining (FCC & ICC)

For FCC, because the successful transfection of the intronic miRNA expression vectors co-expressed a red fluorescent RGFP marker protein with the desired miRNA at a 1:1 ratio, we could directly observe the RGFP under a fluorescent microscopic system (11, 12). For ICC, primary antibodies and immunohistochemical staining kits were obtained from Imgenex (San Diego, Calif.). Immunostaining the active form of ROCK proteins was performed according to the manufacturers' suggestions as reported (6). The Thr-286 site of the ROCK kinase domain was usually masked by an inhibitory Cys/His-rich pleckstrin homology (PH) domain located in the carboxyl (C)-terminus of inactive ROCK. Rho, a small GTPase, bound to a region close to the PH domain and removed this kinase mask, which led to the detection of active ROCK proteins by a ROCK1(thr286) antibody. Since the ROCK1(thr286) antibody was pre-labeled by biotin, alkaline phosphatase-conjugated sheep streptavidin-Fab fragment antibody (Roche) was used as the secondary antibody. Then the bound antibody was detected with Fast Red staining (Roche) for a consistent period of 2 minutes. All positive results were observed under a 100× microscope with whole field scanning and measured at 400× magnification for quantitative analysis by a Metamorph Imaging program (Nikon 80i and TE2000 microscopic quantitation systems).

DNA-Density Flow Cytometry

Cells were trypsinized, pelleted and fixed by re-suspending in 1 ml of pre-chilled 70% methanol in PBS for 1 h at −20° C. The cells were pelleted and washed once with 1 ml of PBS. The cells were pelleted again and resuspended in 1 ml of 1 mg/ml propidium iodide, 0.5 μg/ml RNase in PBS for 30 min at 37° C. Approximately 15,000 cells were then analyzed on a BD FACSCalibur (San Jose, Calif.). Cell doublets were excluded by plotting pulse width versus pulse area and gating on the single cells. The collected data were analyzed using the software package Flowjo using the "Watson Pragmatic" algorithm.

Invasion Assay

Chamber inserts (12-μm pore size; Chemicon, Temecula, Calif.) were coated with 200 μg/ml of matrigel alone or supplemented with 400 μg/ml of HA in phenol red-free-DMEM with 1% L-glutamine and dried overnight under sterile conditions. Cells were harvested, washed, and resuspended in phenol red-free-DMEM to give a final cell density of $1\times10^6$ cells/ml for PC3 and mir-146a-transfected PC3 cells, respectively. Then, five hundred microliters of the resulting cell suspension were dispensed into the top chamber, whereas DMEM-conditioned medium (1.5 ml) was added to the bottom chamber to create a chemotactic gradient. Invasion was measured after overnight incubation at 37° C. for 16 h. Top chambers were wiped with cotton wool, and invading cells on the underside of the membrane were fixed in 100% methanol for 10 min, air dried, stained in cresyl violet for 20 min, and gently rinsed in water. When dry, the cresyl violet stain on membranes was eluted using a 100% ethanol/ 0.2 M NaCitrate (1:1) wash for 20 min and absorbance read at 570 nm using a Precision Microplate Reader (Molecular Dynamics). The percentage of invading cells was calculated by comparison of absorbance in test samples against absorbance determined on membrane inserts that were not wiped (total cells).

Adhesion Assay

Cells were trypsinized, washed in adhesion media [RPMI 1640/0.1% BSA/20 mM HEPES (pH7.4)] and sterile saline once, and resuspended at $1 \times 10^6$ cells/ml in PBS with 10 µM fura-4 acetoxymethyl ester (fluorescent probe, Sigma) for 1 h at 37° C. in the dark. Cells were then pelleted, washed in serum-free medium containing 1% (v/v) of probenecid (100 mM) and incubated for 20 min in adhesion media at 37° C. in the dark to activate the intracellular fluorescent probe. Cells ($3 \times 10^5$ cells/10 were resuspended in adhesion medium and protected from the light until experimentation. Human bone marrow endothelial cells (hBMEC) were seeded at a density of $1 \times 10^5$ cells/ml in 96-well plates and washed with adhesion media before assays as reported (6). Cancer cells were added (300-µl cell suspension/well) to the confluent hBMEC monolayers and incubated for specific times up to 50 min at 37° C. in the presence of 400 µg/ml HA. Non-adherent cells were removed using 2×250 µl washes of adhesion medium. Finally, plates were read in a fluorescent plate reader (Molecular Dynamics) at 37° C. using an excitation wavelength of 485 nm and an emission wavelength of 530 nm.

Statistical Analysis

Results were presented as mean±SE. Statistical analysis of the data was performed by one-way ANOVA. When main effects were significant, the Dunnett's post-hoc test was used to identify the groups that differed significantly from the controls. For pairwise comparison between two treatment groups, the two-tailed student t test was used. For experiments involving more than two treatment groups, ANOVA was performed followed by a post-hoc multiple range test. Probability values of $p<0.05$ were considered significant. All p values were determined from two-tailed tests.

Results

Identification of Differentially Expressed miRNAs in HRPC-Derived Versus Androgen-Dependent Human Prostate Cancer Cell Lines Using miRNA microarray analysis, the inventors consistently detected at least 8 down-regulated and 3 up-regulated miRNAs in androgen-independent human prostate cancer cell lines, such as LNCaP-C81, LNCaP C4-2B and PC3, as compared to those androgen-dependent cell lines, such as LNCaP and PC3-AR9 (FIG. 1). Different androgen responsiveness among these cell lines provided significant insight into the mechanism of androgen receptor (AR)-controlled tumorigenecity in androgen-dependent cancer versus HRPC. For instance, a mutant-type AR, T877A, was highly expressed in LNCaP cells, which showed several fold higher sensitivity to androgen stimulation as compared to the wild-type AR (13). In contrast, C4-2B cells, a LNCaP-derived cell line possessed the same T877A AR but lost some downstream components of the AR signaling pathway, consequently resulting in androgen-independent cell growth (13). Through a different HRPC progression mechanism, PC3 cells possessed all the AR signaling components except AR itself (14). Transgenic expression of a wild-type AR in PC3 cells, namely a PC3-AR9 cell line, restored almost all normal AR responses to androgen stimulation and resulted in about six fold less HA retaining on the cell surface (14). Given that the inventors could compare PC3 to PC3-AR9 and LNCaP to C4-2B to understand the different functionality of wild-type and mutant ARs, respectively, miRNA microarray comparison among these four cell lines might likely shed light on the miRNA-mediated mechanisms in relation to the AR responsiveness.

As shown in FIG. 1, both of the miRNA microarray comparisons between LNCaP C4-2B and original LNCaP as well as PC3 and PC3-AR9 cells showed significant up-regulation of mir-184, mir-361 and mir-424 expression and down-regulation of mir-19b, mir-29b, mir-128b, mir-146a&b, mir-221, mir-222 and mir-663 in HRPC-related LNCaP C4-2B and PC3 cells as compared to androgen-dependent LNCaP and PC3-AR9 cells. Currently, only the mir-184 has been clearly shown to possess oncogenic activities in prostate cancer. A recent study demonstrated that an aberrant splicing variant of androgen receptor, AR23, contained 69 nucleotides of the intron 2 sequence, which separated the two AR zinc fingers required for nuclear entry (15). It suggested that expression of mir-184 might silence its targeted splicing factor 1 (SF1) gene and caused aberrant splicing of the ARs, which impaired the nuclear entry of the resulting AR variants upon dihydrotestosterone (DHT) stimulation, leading to androgen-insensitive cancer transformation and elevated tumorigenecity. Thus, in view of this positively identified miRNA marker in HRPC, the inventors continued to evaluate the tissue-specific expression patterns of mir-184 and mir-146a in human prostate cancer tissue arrays, expecting to correlate the mix-184 and mir-146a expression with the progression of prostate cancer in vivo.

Confirmation of Microarray-Identified miRNA Expressions in Human Prostate Cancer Tissue Arrays In Vivo Prostate carcinoma often shows a heterogeneous and multifocal incidence with diverse clinical and morphologic manifestations. Knowledge of the molecular basis for such heterogeneity is however limited. To accurately distinguish prostate cancer progression, the inventors divided patients' tissue samples into four distinct groups based on their Gleason scores and metastasis status, including: (1) non-cancerous prostate tissues; (2) prostate carcinomas with Gleason scores of 5-6; (3) androgen-independent prostate carcinomas with Gleason scores of 7-8; and (4) metastatic prostate carcinomas with Gleason scores of 9-10. The inventors determined the in vivo expression patterns of the microarray-identified miRNAs of the 4 groups using fluorescent in-situ hybridization (FISH).

Figure 2:
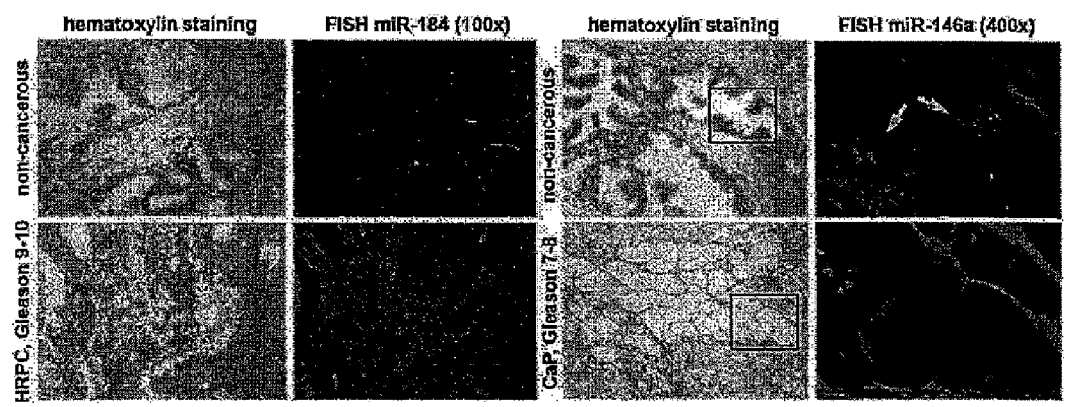
FIG. 2. Fluorescent in-situ hybridization analyses of mir-184 and mir-146a expression in human prostate cancer tissue arrays in vivo. In prostatic epithelium, mir-184 expression was gradually increased corresponding to cancer progression, while mir-146a expression was greatly diminished in most of advanced prostate cancers with Gleason scores over 7. Ratios (upper right corner) showed the positive samples versus the total patient numbers from each cancer stage. Simultaneous elevation of mir-184 and loss of mir-146a expression were observed in over 75% of HRPC epithelium ($p<0.001$; $n=4$), suggesting the significance of miRNA-mediated cancer transformation in vivo.

In addition to the miRNA microarray data which demonstrated a concurrent increase of mir-184 and loss of mir-146a expression in HRPC-related PC3 and LNCaP C4-2B cells in vitro, the inventors found that the FISH results of mir-184 and mir-146a expression in vivo completely matched the microarray-identified patterns in high-grade HRPC compared to androgen-sensitive, non-cancerous prostate epithelium. As shown in FIG. 2, both of the mir-184 and mir-146a were expressed in prostatic epithelium as well as stromal tissues. Following the progression of cancer stages, mir-184 expression was relatively weak in non-cancerous tissues and gradually became intensified in more advanced prostate cancers, particularly in metastatic HRPC. Whereas mir-146a was expressed strongly in non-cancerous prostate epithelium but weakly in stromal area. This strong epithelial expression pattern, however, was gradually lost following the cancer progression. Over 75% of the tested tissue array samples perfectly corresponded with the FISH results, indicating that the concurrent increase of mir-184 and loss of mir-146a expression in HRPC was a prevalent incidence in vivo. Based on this finding, the inventors should be able to use such specific miRNA profiles as cancer stage signatures for predicting prostate cancer progression.

Mir-146a-Mediated ROCK1 Gene Silencing and Inhibition of HA/ROCK1-Mediated PC3 Cell Proliferation In Vitro While the oncogenic mechanism of mir-184 has been recently reported (15), the tumor-suppressor role of mir-146a is still not clear yet. The present invention, provides what is believed to be the first insight into the mir-146a function in regulating prostate cancer progression. ROCK1 was one of the predicted mir-146a target genes, which has been identified to be highly involved in HRPC transformation and metastasis in vivo as well as in HRPC-derived PC3 cells (6). The inventors previous studies have shown that in over 70% of advanced prostate cancers extracellular matrix HA could interact with CD168/CD44 and stimulates ROCK1 signaling, which induces HRPC transformation. The elevated HA content in many solid tumors in vivo has been estimated to be as high as over 100 μg/ml (16). Thus, in the presence of high HA density, mir-146a-mediated ROCK1 silencing played an important role in suppressing HRPC-associated tumorigenecity, such as cancer cell proliferation (anti-apoptosis), invasion and metastasis.

Figure 3:
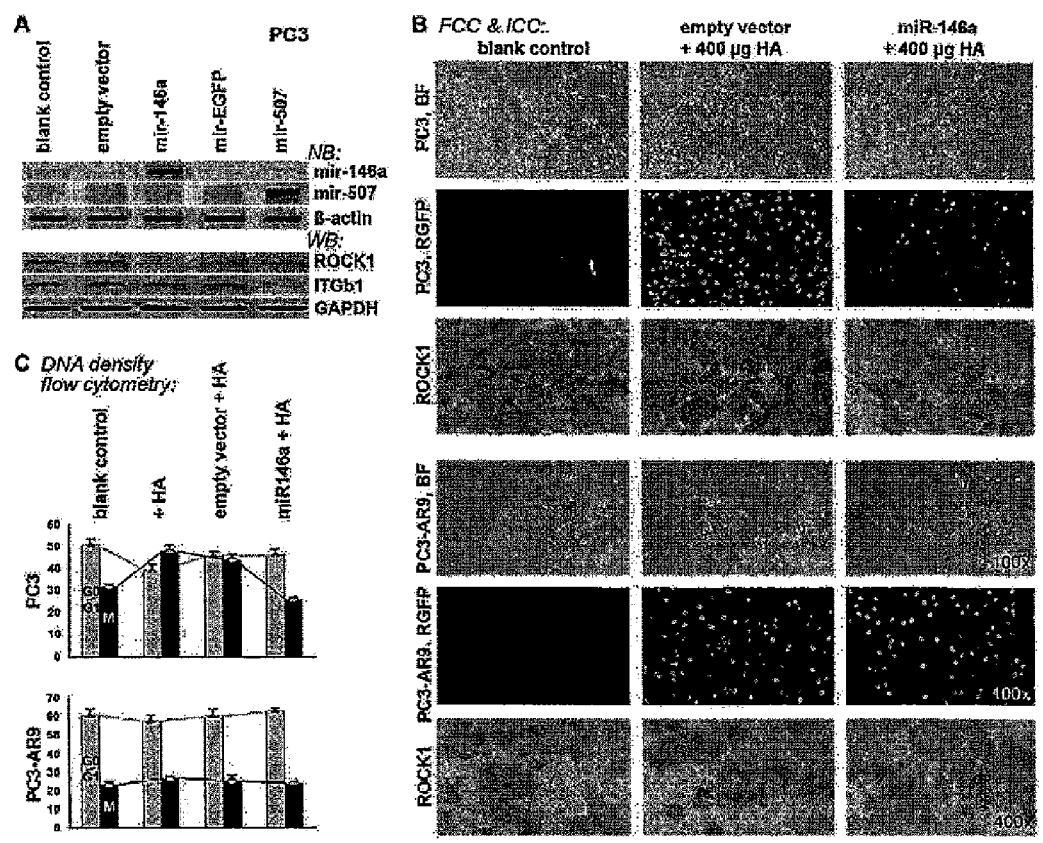
FIG. 3. Mir-146a-mediated ROCK suppression in androgen-independent human prostate cancer PC3 cells. (A) Concurrent Northern blotting (NB) of mir-146a and Western blotting (WB) of ROCK1 levels showed that transfection of mir-146a suppressed over 82% of ROCK1 expression, while other off-target genes, such as integrin β1 (ITGb1) and GAPDH, were not affected ($p<0.001$; $n=4$). (B) Immunocytochemical staining (ICC) of ROCK1 protein in fluorescent-labeled PC3-mir146a cells (FCC). The mix-146-transfected PC3 cells were shown to co-express a fluorescent marker protein, RGFP (middle). In the RGFP-positive PC3-mir146a cells, the ROCK1 protein was markedly reduced, while the PC3 cells transfected with an empty vector showed elevated levels of active ROCK1 after HA stimulation. Cell proliferation rates were changed in response to these ROCK1 alterations, which displayed a much faster cell growth in HA-stimulated PC3 cells than those PC3-mir146a cells, as shown in the result of (C). No significant change was found in PC3-AR9 cells with any tested treatment. (C) Flow cytometry analysis of HA-stimulated cell proliferation ($p<0.05$; $n=4$), showing assignment of cell populations with different DNA contents (y axis) to different cell cycle stages (x axis); from left to right, C (G0/G1 phase), D (S phase) and E (G2/M phase). The first (left) and second (right) peaks represented the levels of G0/G1 and M phase cell populations in the entire cell population, respectively. Bar charts (right) indicated the ratios of different cell populations (x axis) versus different treatments (y axis), including untreated control cells (Ctl), cells treated with 400 µg/ml HA (+HA), cells treated with empty vector and then HA (empty vector+HA), and cells treated with mir-146a-expressing vector and then HA (mir-146a+HA). The white bar refers to the cell population resting in the G0/G1 non-dividing phase, whereas the black bar represents the mitotic (M) cell population.

To test the mir-146a effects on these tumorigenetic aspects, the inventors chose a vector-based miRNA knock-in approach instead of antisense oligonucleotide-mediated miRNA knockout methods in order to prevent any potential cytotoxicity and transfection inconsistency. The inventors have developed a Pol-II-mediated intronic miRNA expression system and successfully demonstrated its special RNAi effects in many vertebrate models (17, 18). Using this intronic miRNA expression system, several transgenic loss-of-gene-function in zebrafish, chicken and mice have been established for studying various human diseases and neuropathological disorders (18). Because intronic miRNA biogenesis had to be coordinately regulated by intracellular Pol-II transcription, RNA splicing and nonsense-mediated RNA decay (NMD) mechanisms, the gene silencing effects obtained were proven to be more specific, controllable and more effective than the antisense oligonucleotide approach (17). Given that loss of mir-146a was observed in PC3 cells, which have been shown to present very high HA/ROCK-mediated HRPC tumorigenecity, it would be a good model to reveal the gain-of-function of mix-146a in PC3 cells. As shown in FIG. 3A, it was observed that vector-based transgenic expression of the native mir-146a precursor significantly knocked down over 82% 3% of ROCK1 expression in PC3 cells, while other off-target genes, such as integrin β1 (ITGb1) and GAPDH, were not affected. The inventors also demonstrated that ITGb1 was an effective target for mir-507 rather than mir-146a. These results confirm the fact that mir-146a is able to trigger a strong and specific gene silencing effect on ROCK1 expression.

To further assess the mir-146a-mediated ROCK1 knockdown effect on PC3-related HRPC tumorigenecity, the inventors performed cell counting and DNA-density flow cytometry analyses to measure the changes of cell proliferation rates and mitotic cell populations. FIG. 3B showed that the mix-146a-mediated, ROCK1-depleted PC3 cells, namely PC3-mir146a, grew much slower than the original PC3 cells with or without empty vector transfection, even in the presence of HA stimulation. The cell number duplication rate of PC3-mir146a was very similar to that of PC3-AR9 cells; however, PC3-AR9 cell growth did not affected by the mix-146a transfection. Since the miRNA microarray analysis shows abundant mir-146a expression in the PC3-AR9 cells, mir-146a might play an important role in regulating PC3 cell growth. To support these findings, cell-cycle analysis using DNA-density flow cytometry showed a 50% reduction of HA-stimulated cell proliferation in PC3-mir146a cells, whereas only 6% reduction occurred in the PC3 cells with empty-vector transfection (FIG. 3C). In the presence of HA, the mitotic cell population (the M phase) was decreased from 48.5%±3.1% to 24.4%±1.6% (50% loss) in PC3 cells, whereas that of PC3-AR9 cells remained almost the same from 23.7%±1.3% to 21.7%±1.7%, suggesting an inhibitory role of mir-146a in regulating PC3 cell growth via ROCK1 knockdown.

Mir-146a-Mediated Suppression of PC3 Cell Invasion and Metastasis

Figure 4:
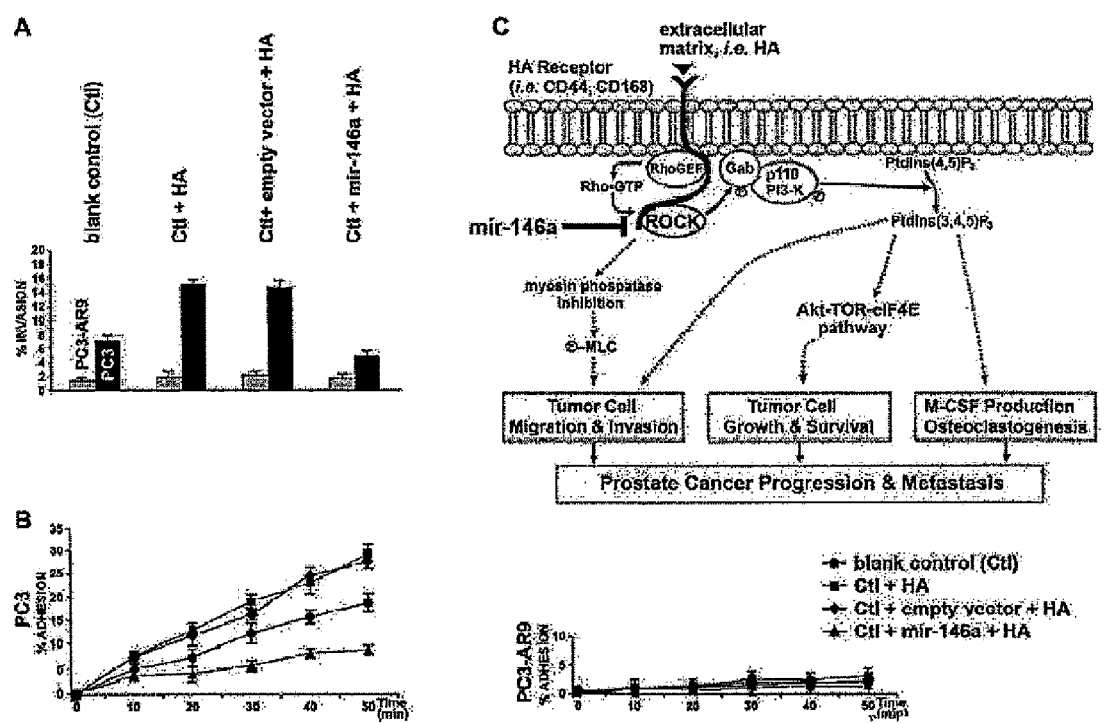
FIG. 4. Characterization of mir-146a-suppressed ROCK effects on HA-dependent cancer cell Invasion and metastasis to hBMEC in androgen-independent PC3 and androgen-dependent PC3-AR9 cells. (A) Functional analysis of mir-146a-suppressed tumor invasion in matrigel chambers ($p<0.05$; $n=4$). Black and white bars referred to PC3 and PC3-AR9 cells, respectively. In the presence of high HA density, a significant increase of tumor invasion was detected in PC3 cells (Ctl+HA), whereas mir-146a-mediated ROCK1 suppression in PC3-mir146a cells (Ctl+mir-146a+HA) could completely reverse this tumorigenetic effect. Transfection of empty vector in PC3 cells (Ctl+empty vector+HA) did not provide any suppression effect on cancer cell invasion. No significant change was observed in PC3-AR9 cells of all treatments. (B) Comparison of cell adhesion to the hBMEC monolayer between PC3 and PC3-AR9 cells ($p<0.05$; $n=6$). The x and y axes referred time duration after treatments and cell population, respectively. Within 50 min, over 29% of PC3 cell population adhered to the hBMEC monolayer after HA treatment (square mark) as compared with a 17% adhesion rate in PC3 cells without any treatment (circle mark). Mir-146a-mediated ROCK1 suppression in PC3-mir146a cells (triangle mark) greatly reduced the HA-stimulated cell adhesion rate from 29% to 7% (76% reduction). PC3-AR9 cells responded weakly to all treatments and barely showed any adhesion to hBMEC (left chart). (C) Three mechanisms have been proposed for HA-mediated ROCK signaling in HRPC transformation (6), including direct MLC phosphorylation to increase cell migration and invasion (route 1), activation of the PI3K-mediated Akt/TOR/eIF4E signaling pathway that supports cancer cell proliferation and anti-apoptosis (route 2), and augmentation of M-CSF cytokine production to facilitate osteolytic metastasis (route 3). In all three pathways, mir-146a functions as a tumor suppressor gene by directly suppressing ROCK1 oncogene expression to prevent the tumorigenetic effects of HA-mediated ROCK signaling in prostate cancer.

To ascertain the tumor-suppressor function of mir-146a in prostate cancer invasion and metastasis, the inventors used matrigel cell invasion assays to test PC3-mir146a cell adhesion to human bone marrow endothelial cell (hBMEC) monolayers. The matrigel cell invasion assays showed that HA stimulation elevated the invasive cell population of PC3 from 6.7%±1.0% to 15.4%±1.1% (130% enhancement), whereas ROCK1-depleted PC3-mir146a cells presented no such a stimulatory effect (34% reduction) (FIG. 4A). Because previous studies have found that HA markedly promoted the invasiveness and metastasis of HRPC-derived PC3 cells mainly through the CD168-ROCK1 signaling pathway, blockade of ROCK1 expression by mir-146a in PC3-mir146a cells might be sufficient to prevent the tumorigenecity of PC3. Coincidentally, a similar result was observed in the cell adhesion assays with hBMEC. As shown in FIG. 4B, a significant increase of PC3 cell adhesion to hBMEC was detected after HA stimulation, whereas PC3-mir146a showed no such a response to the same HA treatment. Within 50 minutes, over 29% of HA-stimulated PC3 cells adhered to hBMEC in comparison with 17% in blank controls (70% enhancement). In contrast, PC3-mir146a cells responded reversely to HA stimulation and showed only a 7% adhesion rate to hBMEC (59% reduction from controls). Interestingly, the mir-146a-expressing PC3-AR9 cells presented neither invasiveness nor metastasis activities in all treatments, suggesting that mir-146a might be responsible for withdrawing the HA/ROCK-mediated invasiveness and metastasis of androgen-dependent prostate cancer cells. Therefore, loss of mir-146a regulation in androgen-independent PC3 cells caused HRPC-associated cancer invasiveness and metastasis.

Discussion

The inventors' previous findings have established that HA-stimulated ROCK1 signaling pathway was responsible for over 70% of HRPC transformation in vivo and in androgen-independent PC3 cells, resulting in dramatic elevation of androgen-independent cancer cell proliferation, invasion and metastasis, as shown in FIG. 4C. The present study added more evidence in the deregulation of HA-stimulated ROCK1 signaling by loss of mir-146a function in androgen-independent prostate cancer cells. The inventors found that loss of mix-146a frequently occurred in androgen-independent PC3 and LNCaP C4-2B cell lines as well as in over 75% of advanced and metastatic prostate carcinomas in vivo. Transfection of mir-146a into PC3 cells was able to restore the mir-146a-mediated ROCK1 gene silencing and thus significantly decreased the HA/ROCK-dependent tumorigenecity, in terms of markedly reduced cancer cell proliferation, invasion and adhesion to hBMEC monolayers. Taken together, all these findings indicated a tumor suppressor role of mir-146a in preventing HA/ROCK-mediated cancer transformation in human prostate epithelium. Further, in view of the inventors' miRNA microarray data, there were more miRNAs not only concurrently but also consistently involved in the processes of prostate cancer transformation.

Many modifications and variation of the invention as hereinbefore set forth can be made without departing from the spirit and scope thereof and therefore only such limitations should be imposed as are indicated by the appended claims.

All patent and literature references cited in the present specification are hereby incorporated by reference in their entirety.

REFERENCES

The following references are cited herein. The entire disclosure of each reference is relied upon and incorporated by reference herein.

1. Reis E M, Nakaya H I, Louro R, Canavez F C, Flatschart A V, Almeida G T, Egidio C M, Paquola A C, Machado A A, Festa F. et al. (2004) Antisense intronic non-coding RNA levels correlate to the degree of tumor differentiation in prostate cancer. *Oncogene*, 23, 6684-6692.
2. Porkka K P, Pfeiffer M J, Waltering K K, Vessella R L, Tammela T L, Visakorpi T. (2007) MicroRNA expression profiling in prostate cancer. *Cancer Res.*, 67, 6130-6135.
3. Volinia S, Calin G A, Liu C G, Ambs S, Cimmino A, Petrocca F, Visone R, Iorio M, Roldo C, Ferracin M. et al. (2006) A microRNA expression signature of human solid tumors defines cancer gene targets. *Proc Natl Acad Sci USA.*, 103, 2257-2261.
4. Esquela-Kerscher. A. and Slack. F. J. (2006) Oncomirsd microRNAs with a role in cancers. *Nat Rev Cancer*, 6, 259-269.
5. Lagos-Quintana M, Rauhut R, Yalcin A, Meyer J, Lendeckel W, Tuschl T. (2002) Identification of tissue-specific microRNAs from mouse. *Curr Biol.*, 12, 735-739.
6. Lin, S. L., Chang, D. and Ying, S. Y. (2007) Hyaluronan stimulates transformation of androgen-independent prostate cancer. *Carcinogenesis*, 28, 310-320.
7. Somlyo, A. V., Phelps, C., Dipierro, C., et al. (2003) Rho kinase and matrix metalloproteinase inhibitors cooperate to inhibit angiogenesis and growth of human prostate cancer xenotransplants. *FASEB J.*, 17, 223-234.
8. Bourguignon, L. Y. W., Singleton, P. A., Zho, H. and Diedrich, F. (2003) Hyaluronan-mediated CD44 interaction with RhoGEF and Rho kinase promotes Grb2-associated binder-1 phosphorylation and phosphatidylinositol 3-kinase signaling leading to cytokine (macrophage-colony stimulating factor) production and breast tumor progression. *J. Biol. Chem.*, 278, 29420-29434.
9. Rodriguez-Viciana, P., Warne, P. H., Vanhaesbroeck, B., Waterfield, M. D. and Downward, J. (1996) Activation of phosphoinositide 3-kinase by interaction with Ras and by point mutation. *EMBO J.*, 15, 2442-2451.
10. De Benedetti, A. and Graff, J. R. (2004) eIF-4E expression and its role in malignancies and metastases. *Oncogene*, 23, 3189-3199.
11. Lin, S. L., Chang, D., Wu, D. Y. and Ying, S. Y. (2003) A novel RNA splicing-mediated gene silencing mechanism potential for genome evolution. *Biochem Biophys Res Commun.*, 310, 754-760.
12. Lin, S. L. and Ying, S. Y. (2005) Gene silencing in vitro and in vivo using intronic microRNAs. Shao-Yao Ying (Ed.) *MicroRNA protocols*, Humana press, Totowa, N.J., pp 295-312.
13. Grossmann, M. E., Huang, H. and Tindall, D. J. (2001) Androgen receptor signaling in androgen-refractory prostate cancer. *J the Natl Cancer Institute*, 93, 1687-1697.
14. Litvinov, I V., Antony, L., Dalrymple, R. B., Cheng, L. and Isaacs, J. T. (2006) PC3, but not DU145, human prostate cancer cells retain the coregulators required for tumor suppressor ability of androgen receptor. *Prostate*, 66, 1329-1338.
15. Jagla M, Feve M, Kessler P, Lapouge G, Erdmann E, Serra S, Bergerat J P, Ceraline J. (2007) A splicing variant of the androgen receptor detected in a metastatic prostate cancer exhibits exclusively cytoplasmic actions. *Endocrinology*, 148, 4334-4343.
16. Paszek M J, Zahir N, Johnson K R, Lakins J N, Rozenberg G I, Gefen A, Reinhart-King C A, Margulies S S, Dembo M, Boettiger D. et al. (2005) Tensional homeostasis and the malignant phenotype. *Cancer Cell*, 8, 241-254.
17. Lin S L and Ying S Y. (2007) Recent progress of the polymerase II-mediated intronic microRNA expression system. Gaur R K and Rossi J (Eds.) *Regulation of Gene Expression by Small RNAs*. CRC press, Florida.
18. Lin S L, Chang S J E, Ying S Y. (2006) Transgene-like animal model using intronic microRNAs. *Methods Mol Biol.*, 342, 321-334.

What is claimed is:

1. A method of preventing or inhibiting the progression of advanced or metastatic of prostate cancer in a subject, comprising:
    administering to the subject an effective amount of one or more miRNAs capable of inhibiting hyaluronan (HA)-mediated activation of Rho-activated protein kinase (ROCK) signal transduction pathway in said subject, wherein said miRNAs include at least mir-146a.
2. The method according to claim 1, wherein said miRNAs are selected from the group consisting of mir-184, mir-361, mir-424, mir-19b, mir-29b, mir-128b, mir-146b, mir-221, mir-222, and mir-663.
3. The method according to claim 1, wherein said miRNA is mir-146a.
4. The method according to claim 1, wherein said cancer is androgen-dependent or androgen-independent.
5. A method of treating advanced or metastatic cancer in a subject suffering from prostate cancer, comprising:
    administering to said subject one or more miRNAs that include at least mir-146a.
6. The method according to claim 5, wherein said miRNAs are selected from the group consisting of mir-184, mir-361, mir-424, mir-19b, mir-29b, mir-128b, mir-146b, mir-221, mir-222, and mir-663.
7. The method according to claim 5, wherein said prostate cancer is androgen-dependent prostate cancer.
8. The method according to claim 5, wherein said prostate cancer is androgen-independent prostate cancer.

* * * * *